United States Patent [19]

Kaplan et al.

[11] Patent Number: 4,626,551
[45] Date of Patent: Dec. 2, 1986

[54] HOMOGENEOUS LIQUID PHASE PROCESS FOR MAKING ALKANE POLYOLS

[75] Inventors: Leonard Kaplan; Wellington E. Walker, both of Charleston, W. Va.

[73] Assignee: Union Carbide Corporation, Danbury, Conn.

[21] Appl. No.: 364,221

[22] Filed: Apr. 1, 1982

Related U.S. Application Data

[63] Continuation of Ser. No. 223,648, Jan. 9, 1981, abandoned, which is a continuation of Ser. No. 138,973, Apr. 10, 1980, abandoned, which is a continuation of Ser. No. 618,021, Sep. 30, 1975, abandoned.

[51] Int. Cl.$^4$ ............................................. C07C 27/06
[52] U.S. Cl. ................................................... 518/701
[58] Field of Search ........................................ 518/701

[56] References Cited

U.S. PATENT DOCUMENTS

3,081,357  3/1963  Alderson et al. .
3,833,634  9/1974  Pruett et al. .
3,855,307 12/1974  Rony .
3,944,588  3/1976  Kaplan .
3,957,857  5/1976  Pruett et al. .

OTHER PUBLICATIONS

Martinengo et al, Gazz, 102 (1972), 344–354.

Primary Examiner—Howard T. Mars
Attorney, Agent, or Firm—Steven T. Trinker

[57] ABSTRACT

This invention relates to the manufacture of valuable alkane polyols by reacting oxides of carbon, such as carbon monoxide, with hydrogen in the presence of a rhodium carbonyl complex in homogeneous liquid phase mixture using a solvent mixture of tetraglyme and a sulfolane.

1 Claim, No Drawings

HOMOGENEOUS LIQUID PHASE PROCESS FOR MAKING ALKANE POLYOLS

This application is a continuation of our prior U.S. application: Ser. No. 223,648, filed 1-9-81 which is a continuation of application Ser. No. 138,973, filed 4-10-80 which is a continuation of application Ser. No. 618,021, filed 9-30-75 all abandoned.

This invention relates to the manufacture of alkane polyols and in particular is concerned with a manufacture, as the most valuable component, of ethylene glycol. The process of this invention constitutes an improvement of the process described and claimed in U.S. Pat. No. 3,833,634, patented Sept. 3, 1974, and the process described in copending application Ser. No. 462,109, filed Apr. 18, 1974.

The process described in the aforementioned patent and patent application involves the reaction of hydrogen and oxides of carbon in the presence of a rhodium carbonyl complex catalyst for the production of the aforementioned alkane polyols. There is described in copending application Ser. No. 537,885, filed Jan. 2, 1975, a process for making the aforementioned alkane polyols utilizing the rhodium carbonyl complex catalysts as described in the previously mentioned patent and patent application where the reaction is effected in a homogeneous liquid phase mixture using tetramethylene sulfone as the prime solvent for effecting the reaction. The patent application speaks of certain distinct advantages accruing from the use of such a solvent, the most important one of which is that such solvents help to avert the loss of catalyst during the reaction.

The aforementioned patent and patent application Ser. No. 462,109, describe the same homogeneous liquid phase process utilizing, in a specific instance, tetraglyme as the solvent. Tetraglyme is an accepted abbreviation for the chemical dimethyl ether of tetraethylene glycol.

It has been determined, quite unexpectedly, that by using a mixture of tetraglyme and sulfolane it is possible to obtain higher rates of formation of the alkane polyol, and one is able to operate, if desired, the process more conveniently and at higher temperatures than is possible from operating the same process utilizing instead only tetraglyme or sulfolane as the solvent.

The use of this solvent mixture in a homogeneous liquid phase reaction provides, at essentially any of the operative temperatures and pressures, higher rates of ethylene glycol formation than would be obtainable from the use of either one of the solvents under the same temperature and pressure conditions, assuming that all other ingredients including promoters are the same. In addition, the use of this solvent mixture in such a reaction allows one to take advantage of the fact that as the temperature of the reaction is increased one is able to enhance the rate constant of alkane polyol formation. A further advantage is that this mixture lessens, when used in the reaction, the potential adverse effects which result from the use of sulfolane at temperatures where, when used alone as a solvent, its instability adversely affects catalyst activity.

This improved process is effected under the temperature and pressure conditions defined in the aforementioned patent and patent application. Thus, the process can be conducted at a temperature between about 100° C. to about 375° C. and at a pressure between about 500 pounds per square inch absolute (psia) to about 50,000 psia. The ratio of tetraglyme and sulfolane that one employs in the solvent mixture providing the homogeneous liquid phase reaction mixture is predicated upon the conditions of the reaction. As a guideline, it is desired that such solvent ratio be selected to provide a rate of formation of the alkane polyol which is greater would be obtained under the same conditions of reaction in either of the solvents.

This ratio of tetraglyme and sulfolane, hereinafter be referred to as the "solvent ratio", may range from 1 to 20 to 20 to 1, determined on a volume basis. However, it is to be emphasized that in any reaction system, such factors as the ratio of carbon monoxide to hydrogen, temperature and pressure selected, concentrations of added components such as catalysts and promoters, the nature of the promoter, play a role in determining what solvent ratio is most effective. In one system the volume ratio of tetraglyme to sulfolane may be optimum at a value of 1 whereas in another the optimum solvent ratio is 2. This statement is made to emphasize the point that when selecting the appropriate solvent ratio one will be required to explore in a number of experiments in a given reaction system a number of ratios such that the optimum solvent ratios can be determined.

The term sulfolane as used herein and in the claims is intended to cover tetramethylene sulfone and substituted tetramethylene sulfone which provide essentially the same advantages as a result of their solvent characteristics as tetramethylene sulfone. Illustrative of substituted sulfolanes which are of a kind that may be suitable as a cosolvent with tetraglyme in the practice of this invention are those which are characterized by the following formula:

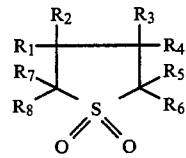

wherein each of $R_1$ through $R_8$ is at least one of hydrogen; hydroxyl; straight or branched chain alkyl, preferably having from 1 to 12 carbon atoms, most preferably 1 to 6 carbon atoms in the alkyl chain, such as methyl, ethyl, isopropyl, butyl, octyl, dodecyl and the like; a cycloaliphatic group including the monocyclic and bicyclic groups such as cyclopentyl, cyclohexyl, bicyclo[2.2.1]heptyl, and the like; or an aryl, alkyl-aryl, or aralkyl group such as phenyl, naphthyl, xylyl, tolyl, benzyl, beta-phenylethyl and the like; an ether of the formula —O—R′ wherein R′ may be aryl or lower alkyl having from 1 to 12 carbon atoms, preferably 1 to 4 carbon atoms in the alkyl chain; an alkylene or polyalkylene ether of the formula —$(OC_nH_{2n})_x$—OR″ wherein n has an average value of from 1 to about 4, x has an average value of from 1 to about 150, preferably 1 to about 20, most preferably 1 to about 4, and R″ may be hydrogen or alkyl having from 1 to 6 carbon atoms in the alkyl chain, such as poly(oxyethylene), poly(oxypropylene), poly(oxyethylene-oxypropylene), alkylene and polyalkylene glycols and lower alkyl ethers thereof; a carboxylate group of the formula:

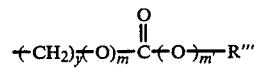

wherein y may have any value between 0 and 12, m and m' may be zero or one provided that when either m or m' is one the other is zero, and R''' may be a lower alkyl group having from 1 to 12 carbon atoms, preferably from 1 to 4 carbon atoms, or aryl; provided that not all of the $R_{1-8}$'s are hydrogen.

Preferably the sulfolane used in the practice of the present invention is tetramethylene sulfone, i.e., tetrahydrothiophene-1,1-dioxide. In those instances where it may be desirable to use a substituted sulfolane those substituted in the 3 or 3,4 positions of the sulfolane ring are preferred.

The rhodium carbonyl complexes suitable for use in the practice of the present invention are those wherein the complex is at least one of (1) rhodium in complex combination with carbon monoxide, (2) rhodium in complex combination with carbon monoxide and hydrogen, (3) rhodium in complex combination with carbon monoxide and at least one Lewis base, (4) rhodium in complex combination with carbon monoxide, hydrogen and at least one Lewis base, and (5) mixtures thereof.

Moreover, the rhodium carbonyl complexes of this invention may be in the form of rhodium carbonyl clusters. P. Chini, in a review article entitled "The Closed Metal Carbonyl Clusters" published in Review (1968), Inorganica Chimica Acta, pages 30-50, states that a metal cluster compound is "a finite group of metal atoms which are held together entirely, mainly, or at least to a significant extent, by bonds directly between the metal atoms even though some nonmetal atoms may be associated intimately with the cluster". The rhodium carbonyl cluster compounds of this invention contain rhodium bonded to rhodium or rhodium bonded to another metal, such as cobalt, and/or iridium. The preferred rhodium carbonyl cluster compounds of this invention are those which contain rhodium-rhodium bonds. These compounds desirably contain carbon and oxygen in the form of carbonyl (—C—O), in which the carbonyl may be "terminal", "edge-bridging", and/or "face-bridging". They may also contain hydrogen and carbon in forms other than carbonyl. The structures disclosed at columns 2 and 3 of U.S. Pat. No. 3,957,857 to Pruett, et al., issued may 18, 1976, are illustrative of what is believed to be the structures of two distinct rhodium carbonyl clusters and both are suitable for use in this invention.

The structures of the rhodium carbonyl clusters may be ascertained by X-ray crystal diffraction, nuclear magnetic resonance (NMR) spectra, or infrared spectra as disclosed in the article entitled "Synthesis and Properties of the Derivatives of the $[Rh_{12}(CO)_{13}]^{2-}$ Anion" by P. Chini and S. Martinengo; appearing in Inorganica Chimica Acta, 3:2 pp299-302, June (1969). Of particular analytical utility in the present invention is the use of infrared spectroscopy which allows for characterization of the particular rhodium carbonyl complex present during the operation of the process of the present invention.

The rhodium carbonyl complex is, as characterized above, a rhodium containing compound in which the rhodium is complexed with CO. This can be achieved with just carbon monoxide or in addition to the carbon monoxide there may be included hydrogen and/or organic or inorganic Lewis base promoters to create the complex. In the last case, "complex" means a coordination compound formed by the union of one or more electronically rich molecules or atoms capable of independent existence with one or more electronically poor molecules or atoms, each of which is also capable of independent existence. The precise role of these Lewis bases in the reaction of the present invention is not fully appreciated at present. They may be functioning as ligands and/or forming counter-ions under the reaction conditions of the present process or they may be functioning just merely as Lewis bases and neutralizing or tying up a molecular species which if allowed to remain "free" or in its non-base-bound state would adversely affect the productivity of the present invention.

Organic Lewis bases which are suitable in the practice of the present invention contain at least one Lewis base oxygen atom and/or one Lewis base nitrogen atom said atoms possessing a pair of electrons available for the formation of coordinate bonds. In suitable embodiments the organic Lewis bases contain from 1 and upwards to 4 Lewis base atoms, preferably from 1 to 3 such atoms, and most preferably 1 or 2 Lewis base atoms. These organic Lewis bases are said to be multidentate or polydentate, that is to say, they are bidentate, tridentate, or quadridentate, depending on whether 2, 3 or 4 Lewis base atoms are involved.

Those organic Lewis bases which contain at least one Lewis base nitrogen atom plus at least one Lewis base oxygen atom will oftentimes hereinafter be referred to as "organic aza-oxa" Lewis bases.

Suitable organic nitrogen Lewis bases ("aza" only) most generally contain carbon, hydrogen, and nitrogen atoms. Suitable organic oxygen Lewis bases most generally contain carbon, hydrogen, and oxygen atoms. Suitable organic aza-oxa Lewis bases most generally contain carbon, hydrogen, oxygen, and nitrogen atoms. The carbon atoms can be acyclic and/or cyclic such as aliphatic, cycloaliphatic, aromatic (including fused and bridged) carbon atoms, and the like. Preferably, the organic Lewis bases contain from 2 to 60, most preferably 2 to 40 carbon atoms. The nitrogen atoms can be in the form of imino (—N═), amino (—N—), nitrilo (N≡), etc. Desirably, the Lewis base nitrogen atoms are in the form of imino nitrogen and/or amino nitrogen. The oxygen atoms can be in the form of groups such as hydroxyl (aliphatic or phenolic), carboxyl

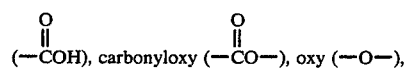 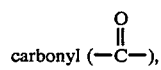

etc., all of said groups containing Lewis base oxygen atoms. In this respect, it is the "hydroxyl" oxygen in the

group and the "oxy" oxygen in the

group that are acting as the Lewis base atoms. The organic Lewis bases may also contain other atoms and/or groups such as alkyl, cycloalkyl, aryl, chloro, trialkylsilyl, and the like.

Illustrative organic oxygen Lewis bases include, by way of illustrations, glycolic acid, methoxyacetic acid, ethoxyacetic acid, diglycolic acid, diethyl ether, tetrahydrofuran, dioxane, tetrahydropyran, pyrocatechol, citric acid, 2-methoxyethanol, 2-ethoxyethanol, 2-n-propoxyethanol, 2-n-butylethanol, 1,2,3-trihydroxybenzene, 1,2,4-trihydroxybenzene, 2,3-dihydroxynaphthalene, cyclohexane-1,2-diol, oxetane, 1,2-dimethoxybenzene, 1,2-diethoxybenzene, methyl acetate, ethanol, 1,2-dimethoxyethane, 1,2-diethoxyethane, 1,2-di-n-propoxyethane, 1,2-di-n-butoxyethane, pentane-2,4-dione, hexane-2,4-dione, heptane-3,5-dione, octane-2,4-dione, 1-phenylbutane-1,3-dione, 3-methylpentane-2,4-dione; the mono- and dialkyl ethers of propylene glycol, of diethylene glycol, of dipropylene glycol; and the like.

Illustrative organic aza-oxa Lewis bases include, for example, the alkanolamines, such as, ethanolamine, diethanolamine, isopropanolamine, di-n-propanolamine, and the like; N,N-dimethylglycine, N,N-diethylglycine; iminodiacetic acid, N-methyliminodiacetic acid; N-methyldiethanolamine; 2-hydroxypyridine, 2,4-dihydroxypyridine, 2-methoxypyridine, 2,6-dimethoxypyridine, 2-ethoxypyridine; lower alkyl substituted hydroxypyridines, such as 4-methyl-2-hydroxypyridine, 4-methyl-2,6-dihydroxypyridine, and the like; morpholine, substituted morpholines, such as 4-methylmorpholine, 4-phenylmorpholine; picolinic acid, methyl-substituted picolinic acid; nitrilotriacetic acid, 2,5-dicarboxypiperazine, N-(2-hydroxyethyl)iminodiacetic acid, ethylenediaminetetraacetic acid; 2,6-dicarboxypyridine; 8-hydroxyquinoline, 2-carboxyquinoline, cyclohexane-1,2-diamine-N,N,N',N'-tetraacetic acid, the tetramethyl ester of ethylenediamine-tetraacetic acid, and the like.

Illustrative of the Lewis base nitrogen ("aza") containing compounds suitable for use in the practice of the present invention are ammonia and the amines. Any primary, secondary, or tertiary amine is suitable in the practice of the present invention. This includes the mono-, di-, tri-, and polyamines and those compounds in which the Lewis base nitrogen forms part of a ring structure as in pyridine, quinoline, pyrimidine, morpholine, hexamethylene tetraamine, and the like. In addition any compound capable of yielding an amino nitrogen under the reaction conditions of the present invention is suitable, as in the case of an amide, such as formamide and urea, or an oxime. Further illustrative of these Lewis base nitrogen compounds are ammonia; aliphatic amines such as methylamine, ethylamine, n-propylamine, isopropylamine, octylamine, dodecylamine, dimethylamine, diethylamine, diisoamylamine, methylethylamine, diisobutylamine, trimethylamine, methyldiethylamine, triisobutylamine, tridecylamine, and the like; aliphatic and aromatic di- and polyamines such as 1,2-ethanediamine, 1,3-propanediamine, N,N,N',N'-tetramethylenediamine, N,N,N',N'-tetraethylethylenediamine, N,N,N',N'-tetra-n-propylethylenediamine, N,N,N',N'-tetrabutylethylenediamine, o-phenylenediamine, m-phenylenediamine, p-phenylenediamine, p-tolylenediamine, o-tolidene, N,N,N',N'-tetramethyl-p-phenylenediamine, N,N,N',N'-tetraethyl-4,4'-biphenyldiamine, and the like; aromatic amines such as aniline, 1-napthylamine, 2-naphthylamine, p-toluidine, o-3-xylidine, p-2-xylidine, benzylamine, dipenylamine, dimethylaniline, diethylaniline, N-phenyl-1-naphthylamine, bis-(1,8)-dimethylaminonaphthalene, and the like; alicyclic amines such as cyclohexylamine, dicyclohexylamine, and the like; heterocyclic amines such as piperidine; substituted piperidines such as 2-methylpiperidine, 3-methylpiperidine, 4-ethylpiperidine, and 3-phenylpiperidine; pyridine; substituted pyridines such as 2-methylpyridine, 2-phenylpyridine, 2-methyl-4-ethylpyridine, 2,4,6-trimethypyridine, 2-dodecylpyridine, 2-chloropyridine, and 2-(dimethylamino)pyridine; quinoline; substituted quinolines, such as 2-(dimethylamino)-6-methoxyquinoline; 4,5-phenanthroline; 1,8-phenanthroline; 1,5-phenanthroline; piperazine; substituted piperazines such as N-methylpiperazine, N-ethylpiperazine, 2,N-dimethylpiperazine; 2,2'-dipyridyl, methyl substituted 2,2'-dipyridyl; ethyl-substituted 2,2'-dipyridyl; 4-triethylsilyl-2,2'-dipyridyl; 1,4-diazabicyclo[2.2.-2]octane, methyl substituted 1,4-diazabicyclo[2.2.2]octane, purine and the like.

Illustrative of the inorganic Lewis bases useful in the practice of the present invention are ammonia, hydroxides and halides, such as chloride, bromide, iodide, or fluoride; or mixtures thereof.

Any of the above Lewis bases may be provided to the reaction in compound form or as ligands which are in complex combination with the rhodium carbonyl compound initially charged to the reactor.

The precise role of the rhodium carbonyl complexes, such as the rhodium carbonyl clusters characterized previously, in the reaction of hydrogen with oxides of carbon to produce polyhydric alcohols is not fully appreciated at present. Under the reaction conditions of the present process the carbonyl complexes are believed to be anionic in their active forms. Rhodium carbonyl anions are known to be involved in the following set of reactions as indicated by S. Martinengo and P. Chini, in Gazz. Chim. Ital., 102, 344 (1972) and the references cited therein.

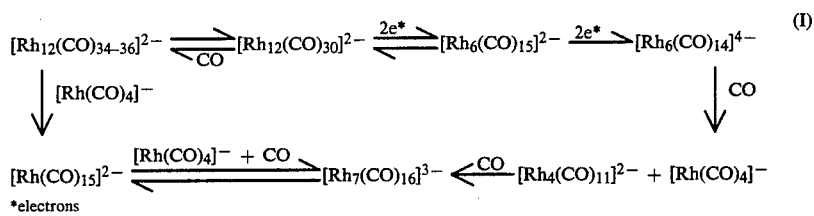

Infrared spectra under reaction conditions of the present process have shown both the $Rh(CO)_4^-$ and $[Rh_{12}(C)_{34-36}]^{2-}$ anions to be present at various concentrations at different times of the reaction. Therefore the set of reactions and equilibria shown in I above may represent the active rhodium carbonyl species responsible for polyhydric alcohol formation or may be merely symptomatic of some further intermediate transitory rhodium carbonyl structure which serves to convert the carbon monoxide and hydrogen to the polyhydric alcohol.

Assuming the active catalytic species is a rhodium carbonyl complex anion, or the formation of the active species under reaction conditions is directly dependent on the existence of these anions, allows one to better explain, in terms of reaction rates, productivity and catalyst stability, the role the sulfone solvents, particularly the tetraethylene sulfones, play in the reaction whereby hydrogen and an oxide of carbon are converted to the polyhydric alcohol. It is believed that the sulfones enhance the reactivity of these rhodium carbonyl complex anions because a "naked", reactive anion is produced. Naked rhodium carbonyl anions are believed to be produced under the reaction conditions of the present process because the sulfone solvent decreases any tendency of the rhodium carbonyl atoms to ion pair, the rhodium carbonyl anions are not strongly solvated, nor is the rhodium strongly complexed by the solvent all of which tend to produce an anion having a high degree of reactivity under the reaction conditions employed.

The novel process is suitably effected over a wide superatmospheric pressure range of from about 800 psia to about 50,000 psia. Pressures as high as 50,000 psia, and higher can be employed but with no apparent advantages attendant thereto which offset the unattractive plant investment outlay required for such high pressure equipment.

In one embodiment of this invention the upper pressure limitation is approximately 16,000 psia. Effecting the present process below about 16,000 psia, especially below about 13,000 psia, and preferably at pressures below about 8000 psia, results in cost advantages which are associated with low pressure equipment requirements. However, when practicing the present invention at pressures below about 12,000 psia, the rate of desired product formation is quite slow and in order to obtain a faster reaction rate and/or higher conversions to the desired product there is provided to the reaction a promoter which may be a salt and/or an organic Lewis base nitrogen compound. In those instances where the Lewis base nitrogen compound is contained as a ligand in the rhodium carbonyl complex charged to the reactor or where anion of the salt promoter charged to the reactor is a rhodium carbonyl complex such as cesium triacontacarbonylrhodate, it may not be necessary to add to the reaction any additional amounts of these promoters. A suitable pressure range for effecting the reaction in the presence of these promoters is from about 1000 psia to about 16,000 psia, preferably from about 4000 to about 16,000 psia.

In a preferred embodiment of the present invention the pressures referred to above represent the total pressures of hydrogen and oxides of carbon in the reactor.

Suitable salts useful in the practice of the present invention at pressures below about 16,000 psia include any organic or inorganic salt which does not adversely affect the production of polyhydric alcohols. Experimental work completed to data indicates that any salt will show this promoter effect under some, but not all, glycol-producing conditions. Illustrative of the salts useful in the practice of the present invention are the ammonium salts and the salts of the metals of Group I and Group II of the Periodic Table (Handbook of Chemistry and Physics—50th Edition) for instance the halide, hydroxide, alkoxide, phenoxide and carboxylate salts such as sodium fluoride, cesium floride, cesium pyridinolate, cesium formate, cesium acetate, cesium benzoate, cesium p-methylsulfonyl benzoate ($CH_3SO_2C_6H_4COO$)Cs, rubidium acetate, magnesium acetate, strontium acetate, ammonium formate, ammonium benzoate and the like. Preferred are the cesium and ammonium carboxylate salts, most preferably their formate, benzoate and para-lower alkyl sulfonyl benzoate salts.

Also useful in the practice of the present invention are organic salts of the following formula:

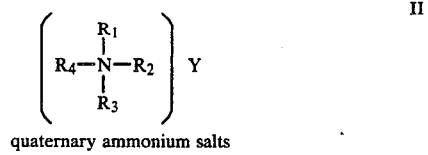

quaternary ammonium salts

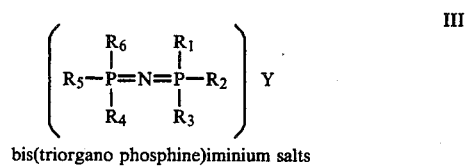

bis(triorgano phosphine)iminium salts wherein $R_1$ through $R_6$ in formulas (II) and (III) above are any organic radicals which do not adversely affect the production of polyhydric alcohols by reacting oxides of carbon with hydrogen in the presence of the aforedefined rhodium carbonyl complex, such as a straight or branched chain alkyl group, having from 1 to 20 carbon atoms in the alkyl chain, such as methyl, ethyl, n-propyl, isopropyl, n-butyl, octyl, 2-ethylhexyl, dodecyl, and the like; or a cycloaliphatic group including the monocyclic and bicyclic groups cyclopentyl, cyclohexyl, and bicyclo[2.2.1]heptyl groups, and the like or an aryl, alkylaryl, or aralkyl group such as phenyl, naphthyl, xylyl, tolyl, t-butylphenyl, benzyl, beta-phenylethyl, 3-phenylpropyl and the like; or a functionally substituted alkyl such as beta-hydroxyethyl, ethoxymethyl, ethoxyethyl, phenoxyethyl, and the like; or a polyalkylene ether group of the formula $-(C_nH_{2n}O)_x-OR$ wherein n has an average value from 1 to 4, x has an average value from 2 to about 150, and R may be hydrogen or alkyl of 1 to about 12 carbon atoms. Illustrative of such polyalkylene ether groups are poly(oxyethylene), poly(oxypropylene), poly(oxyethyleneoxypropylene), poly(oxyethyleneoxybutylene), and the like. Y in formulas II and III above may be any anion which does not adversely affect the production of polyhydric alcohols in the practice of the present invention such as hydroxide; a halide, for instance fluoride, chloride, bromide and iodide; a carboxylate group, such as formate, acetate, propionate, and benzoate and the like; an alkoxide group such as methoxide, ethoxide, phenoxide, and the like; a functionally substituted alkoxide or phenoxide group such as methoxyethoxide, ethoxyethoxide, phenoxyethoxide and the like; a pyridinolate or quinolate group; and others. Preferably Y in formulas II and III, above, is a carboxylate, most preferably formate, acetate and benzoate.

A suitable method for preparing the bis(triorgano phosphine)iminium salts is disclosed in an article by Appel, R. and Hanas, A. appearing in Z. Anorg. u. Allg. Chem., 311, 290, (1961).

Other organic salts useful in the practice of the present invention include the quaternized heterocyclic amine salts such as the pyridinium, piperidinium, morpholinium, quinolinium salts and the like, e.g., N-ethylpyridinium fluoride, N-methylmorpholinium benzoate, N-phenylpiperidinium hydroxide, N,N'-dimethyl-2,2-bipyridinium acetate, and the like.

In one of the embodiments of the present invention, the anion of the above salt promoters may be any of the rhodium carbonyl anions. Suitable rhodium carbonyl anions include $[Rh_6(CO)_{15}]^{2-}$; $[Rh_6(CO)_{15}Y]^-$ wherein Y may be halogen, such as chlorine, bromine, or iodine, $[Rh_6(CO)_{15}(COOR'')]^-$ wherein R'' is lower alkyl or aryl such as methyl, ethyl, or phenyl; $[Rh_6(CO)_{14}]^{2-}$; $[Rh_7(CO)_{16}]^{3-}$; and $[Rh_{12}(CO)_{30}]^{2-}$.

Under reaction conditions where a salt promoter is employed the salt is desirably added with the initial charge of reactants in amounts of from about 0.5 to about 2.0 moles, preferably from about 0.8 to about 1.6 moles, and most preferably from about 0.9 to 1.4 moles of salt for every five atoms of rhodium present in the reaction mixture.

The Lewis base nitrogen promoters may be any of the Lewis base nitrogen or organic aza-oxa Lewis base compounds defined above. Preferably the Lewis base nitrogen promoters are amines. This also includes those compounds where the nitrogen is part of a heterocyclic ring such as the pyridines, pyrmidines, piperidines, morpholines, quinolines and the like. Illustrative of these preferred Lewis base promoters are pyridine, 2,4,6-trimethylpyridine, 4-dimethylaminopyridine, 4-tridecylpyridine, isobutylamine, triethylamine, N-methylpiperidine, N-methylmorpholine, bis-(1,8)-dimethylaminonaphthalene, 1,4-diazabicyclo[2.2.2]octane, and quinuclidine.

Under reaction conditions where a Lewis base nitrogen compound is used as a promoter it is preferably used in amounts from about 0.02 to about 2 equivalents of promoter, most preferably from about 0.1 to about 1 equivalent of promoter, for every mole of rhodium in the reaction mixture. The number of equivalents of promoter is equal to the number of moles of promoter times the number of nitrogen atoms in each molecule.

Mixtures of the above salts and amine low pressure promoters may be used in the practice of the present invention.

The salt and/or Lewis base nitrogen low pressure promoters may be added to the reaction in compound form or there may be added to the reactor any substance capable of generating the salt and/or the amine promoter in situ either prior to or during the reaction conditions of the present invention.

For instance an amide such as formamide, urea, and the like or an oxime may be added to the reactor in place of the amine promoter.

Another and preferred group of low pressure promoters include the trialkanolamine borates, preferably those having the formula:

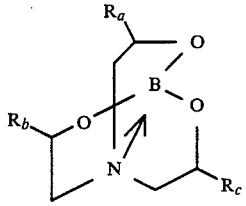

wherein $R_a$, $R_b$, and $R_c$ may be at least one of hydrogen or lower alkyl having from 1 to 12 carbon atoms in the alkyl chain. Most preferably the trialkanolamine borates useful in the practice of the present invention are triethanolamine borate and triisopropanolamine borate.

The quantity of catalyst employed is not narrowly critical and can vary over a wide range. In general, the novel process is desirably conducted in the presence of a catalytically effective quantity of the active rhodium species which gives a suitable and reasonable reaction rate. Reaction proceeds when employing as little as about $1 \times 10^{-6}$ weight percent, and even lesser amounts, of rhodium metal based on the total weight of reaction mixture. The upper concentration limit can be quite high, e.g., about thirty weight percent rhodium, and higher, and the realistic upper limit in practicing the invention appears to be dictated and controlled more by economics in view of the exceedingly high cost of rhodium metal and rhodium compounds. Depending on various factors such as the promoter of choice, the partial pressures of hydrogen and oxides of carbon, the total operative pressure of the system, the operative temperature, the choice of the organic co-diluent, and other considerations, a catalyst concentration of from about $1 \times 10^{-5}$ to about 5 weight percent rhodium (contained in the complex catalyst) based on the total weight of reaction mixture, is generally desirable in the practice of the invention.

The operative temperature which may be employed can vary over a wide range of elevated temperatures. In general, the novel process can be conducted at a temperature in the range of from about 100° C. and upwards to approximately 375° C., and higher. Operative temperatures outside this stated range, though not excluded from the scope of the invention, do not fall within certain desirable embodiments of the invention. At the lower end of the temperature range, and lower, the rate of reaction to desired product becomes markedly slow. At the upper temperature range, and beyond, signs of some catalyst instability are noted. Notwithstanding this factor, reaction continues and polyhydric alcohols and/or their derivatives are produced. Additionally, one should take notice of the equilibrium reaction for forming ethylene glycol:

$$2CO + 3H_2 \rightleftharpoons HOCH_2CH_2OH$$

At relatively high temperatures the equilibrium increasingly favors the left hand side of the equation. To drive the reaction to the formation of increased quantities of ethylene glycol, higher partial pressures of carbon monoxide and hydrogen are required. Processes based on correspondingly higher operative pressures, however, do not represent preferred embodiments of the invention in view of the high investment costs associated with erecting chemical plants which utilize high pressure utilities and the necessity of fabricating equipment capable of withstanding such enormous pressures. Suitable operative temperatures are between about 150° C. to about 320° C., and desirably from about 210° C. to about 300° C.

The novel process is effected for a period of time sufficient to produce the desired polyfunctional oxygen-containing products and/or derivatives thereof. In general, the residence time can vary from minutes to several hours, e.g., from a few minutes to approximately 24 hours, and longer. It is readily appreciated that the residence period will be influenced to a significant extent by the reaction temperature, the concentration and choice of the catalyst, the total gas pressure and the partial pressure exerted by its components, the concentration, and other factors. The synthesis of the desired product(s) by the reaction of hydrogen with an oxide of carbon is suitably conducted under operative conditions which give reasonable reaction rates.

The relative amounts of oxide of carbon and hydrogen which are initially present in the reaction mixture can be varied over a wide range. In general, the mole ratio of $CO:H_2$ is in the range of from about 20:1 to about 1:20, suitably from about 10:1 to about 1:10, and preferably from about 5:1 to about 1:5.

It is to be understood, however, that molar ratios outside the aforestated broad range may be employed. Substances or reaction mixtures which give rise to the formation of carbon monoxide and hydrogen under the reaction conditions may be employed instead of mixtures comprising carbon monoxide and hydrogen which are used in preferred embodiments in the practice of the invention. For instance, polyhydric alcohols are obtained by using mixtures containing carbon dioxide and hydrogen. Mixtures of carbon dioxide, carbon monoxide and hydrogen can also be employed. If desired, the reaction mixture can comprise steam and carbon monoxide.

The novel process can be executed in a batch, semi-continuous, or continuous fashion. The reaction can be conducted in a single reaction zone or a plurality of reaction zones, in series or in parallel, or it may be conducted intermittently or continuously in an elongated tubular zone or series of such zones. The material of construction should be such that it is inert during the reaction and the fabrication of the equipment should be able to withstand the reaction temperature and pressure. The reaction zone can be fitted with internal and/or external heat exchanger(s) to thus control undue temperature fluctuations, or to prevent any possible "runaway" reaction temperature due to the exothermic nature of the reaction. In preferred embodiments of the invention, agitation means to vary the degree of mixing of the reaction mixture can be suitably employed. Mixing induced by vibration, shaker, stirrer, rotatory, oscillation, ultrasonic, etc., are all illustrative of the types of agitation means which are contemplated. Such means are available and well-known to the art. The catalyst may be initially introduced into the reaction zone batchwise, or it may be continuously or intermittently introduced into such zone during the course of the synthesis reaction. Means to introduce and/or adjust the reactants, either intermittently or continuously, into the reaction zone during the course of the reaction can be conveniently utilized in the novel process especially to maintain the desired molar ratios of and the partial pressures exerted by the reactants.

As intimated previously, the operative conditions can be adjusted to optimize the conversion of the desired product and/or the economics of the novel process. In a continuous process, for instance, when it is preferred to operate at relatively low conversions, it is generally desirable to recirculate unreacted synthesis gas with/without make-up carbon monoxide and hydrogen to the reaction. Recovery of the desired product can be achieved by methods well-known in the art such as by distillation, fractionation, extraction, and the like. A fraction comprising rhodium catalyst, generally contained in byproducts and/or normally liquid organic diluent, can be recycled to the reaction zone, if desired. All or a portion of such fraction can be removed for recovery of the rhodium values or regeneration to the active catalyst and can be intermittently added to the recycle stream or directly to the reaction zone.

The active forms of the rhodium carbonyl clusters may be prepared by various techniques. They can be preformed and then introduced into the reaction zone. Alternatively, any of the host of rhodium-containing substances as well as any of the low pressures promoters can be introduced into the reaction zone and, under the operative conditions of the process (which of course includes hydrogen and carbon monoxide), the active rhodium carbonyl cluster can be generated in situ. Illustrative of rhodium-containing substances which can be conveniently introduced or placed in the synthesis zone include, for example, rhodium oxide ($Rh_2O_3$), tetrarhodium dodecacarbonyl, dirhodium octacarbonyl, hexarhodium hexadecacarbonyl ($Rh_6(CO)_{16}$), rhodium(II) formate, rhodium(II) acetate, rhodium(II) propionate, rhodium(II) butyrate, rhodium(II) valerate, rhodium-(III) naphthenate, rhodium dicarbonyl acetylacetonate, rhodium tri(acetylacetonate), rhodium trihydroxide, indenyl-rhodium dicarbonyl, rhodium dicarbonyl (1-phenylbutane-1,3-dione), tris(hexane-2,4-dionato)rhodium(III), tris(heptane-2,4-dionato)rhodium(III), tris(1-phenylbutane-1,3-dionato)rhodium(III), tris(3-methylpentane-2,4-dionato)rhodium(III), tris(1-cyclohexylbutane-1,3-dionato)rhodium(III), triacontacarbonyl rhodium salts and rhodium-containing compounds deposited on porous supports or carriers capable of providing rhodium carbonyls in solution, and others.

The preparation of the rhodium carbonyl complex compounds can be conveniently carried out in the solvent mixture. Tetrarhodium dodecacarbonyl, though of limited solubility, can be added to the solvent in a finely divided form. Any of several of the rhodium-containing compounds illustrated previously can be employed in lieu of tetrarhodium dodecacarbonyl. The organic Lewis bases such as pyridine, or other promoters, such as the aforedefined salt promoters, can also be added thereto. The rhodium carbonyl complex or cluster forming reaction can be effected under a carbon monoxide pressure, with or without $H_2$, of about 1 to 15 atmospheres, and higher, using a temperature of about 30° C. to about 100° C., for a period of time ranging from minutes to a few days, generally from about 30 minutes to about 24 hours. The resulting rhodium carbonyl complex contained in the solvent mixture is catalytically active in this process. In preparing the aforesaid complexes, one can suitably employ from about 0.01 to about 25 moles salt or Lewis base nitrogen promoters per mole of rhodium (contained in the rhodium compound used as a rhodium source). Ratios outside this stated range can be employed especially when it is desirable to use diluent quantities of the low pressure promoters.

The equipment arrangement and procedure which provides the capability for determining the existence of anionic rhodium carbonyl complexes or clusters having defined infrared spectrum characteristics, during the course of the manufacture of polyhydric alcohols from carbon monoxide and hydrogen, pursuant to this invention is disclosed and schematically depicted in U.S. patent application Ser. No. 462,109, filed Apr. 18, 1974, the disclosure of which is incorporated herein by reference.

A particularly desirable infrared cell constructure is described in copending U.S. Pat. No. 3,886,364, issued May 27, 1975 and its disclosure of a preferred cell construction is incorporated herein by reference.

The "oxide of carbon" as covered by the claims and as used herein is intended to mean carbon monoxide and mixtures of carbon dioxide and carbon monoxide, either introduced as such or formed in the reaction. Preferably the oxide of carbon is carbon monoxide.

The reaction of the present invention is conducted in what is believed to be a homogeneous liquid phase, which means that the catalyst, the reaction products and the promoter if present are in solution. Though the reaction to produce alcohols is essentially homogeneous, there may be small amounts of insoluble catalyst particles depending on the reaction conditions employed.

The following examples are merely illustrative and are not presented as a definition of the limits of the inventions.

The sulfolane used in the following examples was purified prior to use according to the method disclosed by E. N. Arnett and C. F. Douty, reported in the Journal of the American Society, 86, 409 (1964).

Other materials used in the following examples possessed the following characteristics: cesium benzoate (recrystallized from $H_2O$, Analysis—Found: C, 32.62; H, 1.90. Calcd. for $C_7H_5O_2Cs$: C, 33.10; H, 1.98). Triisopropanolamine borate (mp. 155°–157.5°); p-$MeSO_2C_6H_4CO_2Cs$; cesium para methylsulfonylbenzoate (recrystallized from $H_2O$, Analysis—Found: C, 28.26; H, 2.05. Calc. for $C_8H_7O_4SCs$: C, 28.90; H, 2.13).

In the examples below, the following procedure was employed:

A 150 ml. capacity stainless steel reactor capable of withstanding pressures up to 7,000 atmospheres was charged with a premix of 75 cubic centimeters (cc) of a specified solvent mixture, a specified amount of rhodium in the form of rhodium dicarbonylacetylacetonate, and specified amounts of one or more of an amine promoter, a borate promoter, and salt promoter. The reactor was sealed and charged with a gaseous mixture containing equal molar amounts of carbon monoxide and hydrogen to a pressure as specified below. Heat was applied to the reactor and its contents; when the temperature of the mixture inside the reactor reached 190° C., as measured by a suitably placed thermocouple, an additional adjustment of carbon monoxide and hydrogen ($H_2$:CO-1:1 mole ratio) was made to bring the pressure back to 8000 psig. The temperatures and pressures were maintained as indicated in the table.

After the reaction was terminated, the vessel and its contents were cooled to room temperature, the excess gas vented and the reaction product mixture was removed. Analysis of the reaction product mixture was made by gas chromatographic analysis using a Hewlett Packard FM TM model 810 Research Chromatograph.

Analysis of the product mixture in terms of ethylene glycol and methanol, are shown in the tables, as well as the rhodium recovery, based on the total rhodium charged to the reactor.

Rhodium recovery was determined by atomic absorption analysis of the contents of the reactor after the venting of the unreacted gases at the end of the reaction. A further analysis was run on a "wash" of the reactor. The wash of the reactor consisted of charging to the reactor 100 cc of the solvent used for that experiment and bringing the reactor and its contents to a temperature of 160° C. and a pressure of 14,000 to 15,000 psig and maintaining these conditions for a period of 30 minutes. The reactor was then cooled and the unreacted gases vented and an atomic absorption analysis for rhodium was run on the reactor's contents. The rhodium recovery values may be characterized as the percent rhodium based on the total rhodium charged to the reactor that is soluble or suspended in the reaction mixture and the wash after the specified reaction time.

EXAMPLES

| Example No. | Sulfolane/ Tetraglyme Ratio(V/V) | Pressure, psi | Temp., °C. | M Moles of RH | Promoters Added And Amount, M Moles |
| --- | --- | --- | --- | --- | --- |
| 1 | 100/0 | 8000 | 240 | 3 | cesium benzoate, 0.65 |
| 2 | 76/24 | 8000 | 240 | 3 | cesium benzoate, 0.65 |
| 3 | 54/46 | 8000 | 240 | 3 | cesium benzoate, 0.65 |
| 4 | 36/64 | 8000 | 240 | 3 | cesium benzoate, 0.65 |
| 5 | 17/83 | 8000 | 240 | 3 | cesium benzoate, 0.65 |
| 6 | 0/100 | 8000 | 240 | 3 | cesium benzoate, 0.65 |
| 7 | 100/0 | 8000 | 240 | 3 | pyridine, 0.63 |
| 8 | 76/24 | 8000 | 240 | 3 | pyridine, 0.63 |
| 9 | 54/46 | 8000 | 240 | 3 | pyridine, 0.63 |
| 10 | 36/64 | 8000 | 240 | 3 | pyridine, 0.63 |
| 11 | 17/83 | 8000 | 240 | 3 | pyridine, 0.63 |
| 12 | 100/0 | 8000 | 260 | 3 | ethylenedimorpholine, 7.0 |
| 13 | 76/24 | 8000 | 260 | 3 | ethylenedimorpholine, 7.0 |
| 14 | 50/50 | 8000 | 260 | 3 | ethylenedimorpholine, 7.0 |
| 15 | 24/76 | 8000 | 260 | 3 | ethylenedimorpholine, 7.0 |
| 16 | 100/0 | 8000 | 240 | 3 | N—methylmorpholine, 5.0 |
| 17 | 76/24 | 8000 | 240 | 3 | N—methylmorpholine, 5.0 |
| 18 | 100/0 | 8000 | 260 | 3 | cesium formate, 0.65; triisoproparolamine borate, 2.5 |
| 19 | 76/24 | 8000 | 260 | 3 | cesium formate, 0.65; triisoproparolamine borate, 2.5 |
| 20 | 50/50 | 8000 | 260 | 3 | cesium formate, 0.65; triisoproparolamine borate, 2.5 |
| 21 | 50/50 | 15000 | 240 | 3 | cesium benzoate, 0.65; triisoproparolamine borate, 2.5 |
| 22 | 13/87 | 15000 | 240 | 3 | cesium benzoate, 0.65; triisoproparolamine borate, 2.5 |
| 23 | 0/100 | 15000 | 240 | 3 | cesium benzoate, 0.65; triisoproparolamine borate, 2.5 |
| 24 | 100/0 | 15000 | 260 | 3 | ethylenedimorpholine, 7.0 |
| 25 | 50/50 | 15000 | 260 | 3 | ethylenedimorpholine, 7.0 |
| 26 | 24/76 | 15000 | 260 | 3 | cesium benzoate, 0.75; pyridine, 1.25 |
| 27 | 0/100 | 15000 | 260 | 1.5 | cesium benzoate, 0.375; pyridine, 1.25 |
| 28 | 50/50 | 15000 | 270 | 1.5 | cesium benzoate, 0.375; pyridine, 1.25 |
| 29 | 24/76 | 15000 | 270 | 1.5 | cesium benzoate, 0.375; pyridine, 1.25 |
| 30 | 50/50 | 15000 | 280 | 1.5 | cesium benzoate, 0.375; pyridine, 1.25 |
| 31 | 24/76 | 15000 | 280 | 1.5 | cesium benzoate, 0.375; pyridine, 1.25 |
| 32 | 0/100 | 12500 | 250 | 6 | cesium benzoate, 1.5; pyridine, 2.5 |
| 33 | 24/76 | 12500 | 250 | 6 | cesium benzoate, 1.5; pyridine, 2.5 |
| 34 | 24/76 | 12500 | 260 | 3 | cesium benzoate, 0.75; pyridine, 1.25 |
| 35 | 50/50 | 12500 | 260 | 3 | cesium benzoate, 0.75; pyridine, 1.25 |

EXAMPLES -continued

| | | | | | | |
|---|---|---|---|---|---|---|
| 36 | 24/76 | 12500 | 270 | 1.5 | cesium benzoate, 0.375; pyridine, 1.25 | |
| 37 | 50/50 | 12500 | 270 | 1.5 | cesium benzoate, 0.375; pyridine, 1.25 | |
| 38 | 60/40 | 12500 | 270 | 1.5 | cesium benzoate, 0.375; pyridine, 1.25 | |
| 39 | 24/76 | 12500 | 270 | 3 | cesium f-methylsulfonylbenzoate, 0.75; triisoproparolamine borate, 2.5 | |
| 40 | 50/50 | 12500 | 270 | 3 | cesium f-methylsulfonylbenzoate, 0.75; triisoproparolamine borate, 2.5 | |

| Example No. | Methanol, M hr$^{-1}$(g) | Ethylene Glycol, M hr$^{-1}$(g) | Rh Recovery, % Reactor | Wash | Gas Uptake (CO + H$_2$), psi | Time of Reaction, hr |
|---|---|---|---|---|---|---|
| 1  | 0.31(3.0) | 0.23(4.2) | 74  | 6  | 2800 | 4.0 |
| 2  | 0.29(2.8) | 0.22(4.0) | 74  | 10 | 3250 | 4.0 |
| 3  | 0.31(3.0) | 0.28(5.2) | 74  | 11 | 2950 | 4.0 |
| 4  | 0.34(3.3) | 0.26(4.9) | 68  | 20 | 2850 | 4.0 |
| 5  | 3.36(3.5) | 0.26(4.9) | 62  | 21 | 3150 | 4.0 |
| 6  | 0.23(2.2) | 0.16(2.9) | 27  | 52 | 2100 | 4.0 |
| 7  | 0.29(2.8) | 0.24(4.5) | 77  | 6  | 3000 | 4.0 |
| 8  | 0.27(2.6) | 0.35(6.5) | 71  | 6  | 3750 | 4.0 |
| 9  | 0.28(2.7) | 0.29(5.3) | 62  | 10 | 3500 | 4.0 |
| 10 | 0.27(2.6) | 0.28(5.2) | 54  | 5  | 2850 | 4.0 |
| 11 | 0.27(2.6) | 0.13(2.4) | 33  | 0  | 1700 | 4.0 |
| 12 | 0.54(5.2) | 0.38(7.1) | 81  | 6  | 5600 | 4.0 |
| 13 | 0.57(5.5) | 0.38(7.1) | 68  | 7  | 6500 | 4.0 |
| 14 | 0.62(6.0) | 0.41(7.7) | 67  | 8  | 6000 | 4.0 |
| 15 | 0.25(2.4) | 0.06(1.1) | 11  | 4  | 2050 | 4.0 |
| 16 | 0.37(3.6) | 0.29(5.3) | 80  | 4  | 4300 | 4.0 |
| 17 | 0.32(3.1) | 0.31(5.7) | 74  | 8  | 4200 | 4.0 |
| 18 | 0.47(4.5) | 0.32(6.0) | 77  | 10 | 4100 | 4.0 |
| 19 | 0.57(5.5) | 0.35(6.5) | 77  | 6  | 4600 | 4.0 |
| 20 | 0.60(5.8) | 0.39(7.2) | 53  | 12 | 5600 | 4.0 |
| 21 | 1.1(1.7)  | 2.1(6.3)  | 102 | 6  | 6250 | 0.65 |
| 22 | 1.6(4.7)  | 2.0(11.7) | 82  | 5  | 8200 | 1.25 |
| 23 | 1.6(3.6)  | 1.4(6.2)  | 69  | 8  | 6100 | 0.96 |
| 24 | 3.1(4.1)  | 2.9(7.4)  | 107 | 6  | 6000 | 0.55 |
| 25 | 2.7(5.4)  | 3.7(14.2) | 91  | 6  | 7300 | 0.83 |
| 26 | 3.1(3.7)  | 4.9(11.4) | 83  | 6  | 7800 | 1.00 |
| 27 | 1.7(3.7)  | 2.0(8.4)  | 0   | 14 | 6000 | 0.45 |
| 28 | 2.7(4.3)  | 3.2(10.6) | 80  | 6  | 6000 | 0.67 |
| 29 | 2.9(2.5)  | 4.1(6.9)  | 76  | 7  | 4050 | 0.36 |
| 30 | 4.3(5.9)  | 4.4(11.8) | 76  | 16 | 6400 | 0.58 |
| 31 | 3.2(5.8)  | 2.7(9.4)  | 39  | 25 | 6000 | 0.76 |
| 32 | 3.1(6.5)  | 2.4(9.8)  | 78  | 11 | 6000 | 0.88 |
| 33 | 5.8(8.0)  | 3.4(9.2)  | 85  | 6  | 6150 | 0.58 |
| 34 | 3.0(5.7)  | 2.6(9.9)  | 92  | 5  | 6000 | 0.80 |
| 35 | 2.9(5.5)  | 2.7(9.8)  | 98  | 6  | 6000 | 0.77 |
| 36 | 0.35(3.5) | 0.25(5.3) | 19  | 36 | 4000 | 4.18 |
| 37 | 1.7(3.8)  | 1.7(7.3)  | 81  | 13 | 4000 | 0.95 |
| 38 | 2.0(4.0)  | 1.7(6.8)  | 78  | 17 | 4000 | 0.85 |
| 39 | 2.4(6.3)  | 1.9(9.8)  | 29  | 41 | 6000 | 1.08 |
| 40 | 2.0(5.5)  | 1.7(8.9)  | 44  | 16 | 6000 | 1.16 |

NOTES TO THE EXAMPLES:

The following examples illustrate that a mixture of sulfolane and tetraglyme leads to a higher rate than does a pure solvent: 1–27 & 32–33.

The following examples illustrate that a mixture of solfolane and tetraglyme leads to a higher rate than does either pure solvent: 1–15.

The following examples illustrate the increase in sulfolane content necessary to achieve good recovery of Rh with increasing temperature: 12–15 vs. 1–11, 26–27 vs. 28–29 vs. 30–31, 32–33 vs 34–35 vs. 36–38.

The following examples illustrate the increase in pressure necessary to achieve good recovery of Rh as temperature increases at constant solvent ratio: (1–15, 18–20) vs. 34–40 vs. 28–31.

Summary:

Rh recovery, and hence rate to glycol, is determined by the three-way interactive effect of solvent ratio, pressure, and temperature. In order that the Rh remain in solution as the temperature is increased, and consequently produce glycol at a higher rate, it is necessary that the sulfolane/tetraglyme ratio be increased or the "solvent ratio" be decreased; this is a more stringent necessity at lower pressure. As the temperature is increased, or pressure decreased, a point will be reached at which high recovery of Rh cannot be brought about by a change in solvent ratio.

What is claimed is:

1. In the homogeneous liquid phase process of producing alkane polyols by the reaction of oxides of carbon and hydrogen in the presence of a rhodium catalyst in which rhodium is complexed with carbon monoxide to provide a rhodium carbonyl complex at a temperature between about 100° C. to about 375° C. and at a pressure between about 1000 psia to about 50,000 psia, the improvement which comprises effecting said reaction in a solvent mixture of tetraglyme and sulfolane under conditions whereby such solvent mixture is essentially inert and the rate of formation of such alkane polyol is greater than would be obtained by effecting said reaction under equal conditions using tetraglyme or sulfolane as the solvent.

* * * * *